United States Patent
Brown (10) Patent No.: US 7,059,509 B2
(45) Date of Patent: Jun. 13, 2006

(54) SURGICAL STAPLING DEVICE

(76) Inventor: Phillip Clay Brown, 2614 Rogers Bluff, San Antonio, TX (US) 78258

(*) Notice: Subject to any disclaimer, the term of this patent is extended or adjusted under 35 U.S.C. 154(b) by 0 days.

(21) Appl. No.: 10/227,947

(22) Filed: Aug. 26, 2002

(65) Prior Publication Data
US 2003/0222118 A1 Dec. 4, 2003

Related U.S. Application Data

(63) Continuation-in-part of application No. 10/156,716, filed on May 28, 2002, now abandoned.

(51) Int. Cl.
*A61B 17/068* (2006.01)

(52) U.S. Cl. .................. 227/176.1; 227/19; 227/82; 227/120

(58) Field of Classification Search ............ 227/175.1, 227/175.3, 176.1, 181.1, 901, 902, 156, 103, 227/120, 127, 128, 139, 19, 109
See application file for complete search history.

(56) References Cited

U.S. PATENT DOCUMENTS

| | | | |
|---|---|---|---|
| 1,271,548 A | 7/1918 | Doig | |
| 2,433,155 A * | 12/1947 | Peterson | 227/127 |
| 2,619,637 A | 12/1952 | Boroughs | |
| 2,707,783 A | 5/1955 | Sullivan | |
| 2,874,384 A | 2/1959 | Krone | |
| 3,618,842 A | 11/1971 | Bryan | |
| 3,643,851 A | 2/1972 | Green et al. | |
| 3,717,294 A | 2/1973 | Green | |
| 3,837,555 A | 9/1974 | Green | |
| 3,873,016 A | 3/1975 | Fishbein | |
| 3,889,865 A * | 6/1975 | Kuypers | 227/109 |
| 3,905,535 A | 9/1975 | Novak et al. | |
| 4,043,504 A | 8/1977 | Hueil et al. | |
| 4,108,306 A | 8/1978 | Samuels et al. | |
| 4,109,844 A | 8/1978 | Becht | |
| 4,179,057 A | 12/1979 | Becht et al. | |
| 4,196,836 A | 4/1980 | Becht | |
| 4,202,480 A | 5/1980 | Annett | |
| 4,204,623 A | 5/1980 | Green | |

(Continued)

OTHER PUBLICATIONS

Color Photo, Left Side View of Product, APPOSE*ULC Disposable Skin Stapler With Auto-Release, Skin Closure 8037-12, Davis+Geck; Containing 35 Wide Stainless Steel Staples 6.9mm×3.8mm, American Cyanamid Company, Wayne, NJ; U.S. Patents (see above) 4,406,392; D269,459; Lot 1108015, MFG Apr. 2001.

(Continued)

*Primary Examiner*—Scott A. Smith
(74) *Attorney, Agent, or Firm*—Akin Gump Strauss Hauer & Feld LLP (57) ABSTRACT

A surgical stapling device having a removable staple cartridge is disclosed. The cartridge includes a first opening in the staple-forming end of the housing member to allow access to the a staple and an aligned second opening to allow the lead staple to move therethrough. The staple cartridge also comprises a fixed blocking surface on the housing member and a traveling blocking surface on a feeder shoe. The traveling blocking surface is sized so that the feeder shoe moves relative to the fixed blocking surface while moving the staple. The feeder shoe is further shaped so that, when the trigger member is actuated when no staples remain in the staple cartridge, the staple former is not blocked by the feeder shoe.

32 Claims, 10 Drawing Sheets

U.S. PATENT DOCUMENTS

| | | | |
|---|---|---|---|
| D269,459 S | 6/1983 | Butter et al. | |
| 4,391,402 A | 7/1983 | Campbell et al. | |
| 4,406,392 A | 9/1983 | Campbell et al. | |
| 4,407,286 A | 10/1983 | Noiles et al. | |
| 4,410,125 A | 10/1983 | Noiles et al. | |
| 4,411,378 A | 10/1983 | Warman | |
| 4,458,835 A | 7/1984 | Li et al. | |
| 4,483,066 A | 11/1984 | Akira | |
| 4,489,875 A | 12/1984 | Crawford et al. | |
| D278,656 S | 4/1985 | Green et al. | |
| 4,558,810 A | 12/1985 | Mulhauser et al. | |
| 4,591,086 A | 5/1986 | Campbell et al. | |
| 4,607,638 A | 8/1986 | Crainich | |
| 4,645,111 A | 2/1987 | Larrabee et al. | |
| 4,662,555 A | 5/1987 | Thornton | |
| 4,669,647 A | 6/1987 | Storace | |
| 4,747,531 A | 5/1988 | Brinkerhoff et al. | |
| 4,796,793 A | 1/1989 | Smith et al. | |
| 4,887,756 A | 12/1989 | Puchy | |
| 5,038,991 A | 8/1991 | Thornton | |
| 5,038,992 A * | 8/1991 | Shiang et al. | 227/120 |
| 5,080,275 A | 1/1992 | Heimerl et al. | |
| 5,100,041 A | 3/1992 | Storace | |
| 5,114,065 A | 5/1992 | Storace | |
| 5,176,306 A | 1/1993 | Heimerl et al. | |
| 5,207,692 A | 5/1993 | Kraus et al. | |
| 5,222,975 A | 6/1993 | Crainich | |
| 5,344,061 A | 9/1994 | Crainich | |
| 5,364,000 A | 11/1994 | Fealey | |
| 5,443,197 A | 8/1995 | Malis et al. | |
| 5,464,300 A | 11/1995 | Crainich | |
| 5,544,802 A | 8/1996 | Cranich | |
| 5,645,567 A | 7/1997 | Crainich | |
| 5,655,697 A * | 8/1997 | Yeh | 227/27 |
| 5,665,097 A | 9/1997 | Baker et al. | |
| 5,765,742 A | 6/1998 | Marks | |
| 5,769,892 A | 6/1998 | Kingwell | |
| 5,810,855 A | 9/1998 | Rayburn et al. | |
| 5,908,149 A | 6/1999 | Welch et al. | |
| 5,938,101 A | 8/1999 | Izuchukwu | |
| 5,941,442 A | 8/1999 | Geiste et al. | |
| 6,045,560 A | 4/2000 | McKean et al. | |
| 6,076,720 A * | 6/2000 | Deng | 227/109 |
| 6,131,790 A | 10/2000 | Piraka | |
| 6,145,728 A | 11/2000 | Marks | |
| 6,202,914 B1 | 3/2001 | Geiste et al. | |
| 6,315,183 B1 | 11/2001 | Piraka | |
| 6,318,616 B1 | 11/2001 | Pasqualucci et al. | |
| 6,402,008 B1 | 6/2002 | Lucas | |

OTHER PUBLICATIONS

Color Photo, Right Side View of Product, APPOSE*ULC Disposable Skin Stapler With Auto-Release, Skin Closure 8037-12, Davis+Geck; Containing 35 Wide Stainless Steel Staples 6.9mm×3.8mm, American Cyanamid Company, Wayne, NJ; U.S. Patents (see above) 4,406,392; D269,459; Lot 1108015, MFGApr. 2001.

Color Photo, Left Side View of Product in Packaging, APPOSE*ULC Disposable Skin Stapler With Auto-Release, Skin Closure 8037-12, Davis+Geck; Containing 35 Wide Stainless Steel Staples 6.9mm×3.8mm, American Cyanamid Company, Wayne, NJ; U.S. Patents (see above) 4,406,392; D269,459; Lot 1108015, MFGApr. 2001.

Color Photo, Back of Packaging, APPOSE*ULC Disposable Skin Stapler With Auto-Release, Skin Closure 8037-12, Davis+Geck; Containing 35 Wide Stainless Steel Staples 6.9mm×3.8mm, American Cyanamid Company, Wayne, NJ; U.S. Patents (see above) 4,406,392; D269,459; Lot 1108015, MFGApr. 2001.

Color Photo, Left Side View of Product, AutoSuture Royal 35W Single Use Skin Stapler, 054887, United States Surgical Corporation; U.S. Patents (see above) 4,407,286; 4,410,125; 4,489,875; D278,656; ; Lot N1K115M, Exp. Nov. 2006.

Color Photo, Right Side View of Product, AutoSuture Royal 35W Single Use Skin Stapler, 054887, United States Surgical Corporation; U.S. Patents (see above) 4,407,286; 4,410,125; 4,489,875; D278,656; ; Lot N1K115M, Exp. Nov. 2006.

Color Photo, Left Side View of Product in Packaging, AutoSuture Royal 35W Single Use Skin Stapler, 054887, United States Surgical Corporation; U.S. Patents (see above) 4,407,286; 4,410,125; 4,489,875; D278,656; ; Lot N1K115M, Exp. Nov. 2006.

Color Photo, Back of Packaging, AutoSuture Royal 35W Single Use Skin Stapler, 054887, United States Surgical Corporation; U.S. Patents (see above) 4,407,286; 4,410,125; 4,489,875; D278,656; ; Lot N1K115M, Exp. Nov. 2006.

Photocopy of Back of Packaging for HH.

Color Photo, Left Side View of Product, 3M Precise™ Vista Disposable Skin Stapler, 3995-35W, Staples 7.1mm×4.1 mm, 3M Health Care, 78-8078-8903-1; Lot Jun. 2006 AN.

Color Photo, Right Side View of Product, 3M Precise™ Vista Disposable Skin Stapler, 3995-35W, Staples 7.1mm×4.1 mm, 3M Health Care, 78-8078-8903-1; Lot Jun. 2006 AN.

Color Photo, Left Side View of Product in Packaging, 3M Precise™ Vista Disposable Skin Stapler, 3995-35W, Staples 7.1mm×4.1 mm, 3M Health Care, 78-8078-8903-1; Lot Jun. 2006 AN.

Color Photo, Back of Packaging, 3M Precise™ Vista Disposable Skin Stapler, 3995-35W, Staples 7.1mm×4.1 mm, 3M Health Care, 78-8078-8903-1; Lot Jun. 2006 AN.

Photocopy of Back of Packaging for LL.

Color Photo, Left Side View of Product, 3M Precise™ Disposable Skin Stapler, MS-25, 3M Health Care, 78-8078-8891-8; Lot Nov. 2006 BC.

Color Photo, Right Side View of Product, 3M Precise™ Disposable Skin Stapler, MS-25, 3M Health Care, 78-8078-8891-8; Lot Nov. 2006 BC.

Color Photo, Left Side View of Product in Packaging, 3M Precise™ Disposable Skin Stapler, MS-25, 3M Health Care, 78-8078-8891-8; Lot Nov. 2006 BC.

Color Photo, Back of Packaging, 3M Precise™ Disposable Skin Stapler, MS-25, 3M Health Care, 78-8078-8891-8; Lot Nov. 2006 BC.

Photocopy of Back of Packaging for PP.

Color Photo, Right Side View of Product, Weck Visistat® Disposable Stapler with 35 Regular Staples. 5.7 mm×3.9 mm Stainless Steel Staples, Weck Closure Systems™, 1998, 220000723 Rev. 00, REF 528135, U.S. Patents (see above) 4,662,555 and 5,038,991.

Color Photo, Left Side View of Product, Weck Visistat® Disposable Stapler with 35 Regular Staples, 5.7 mm×3.9 mm Stainless Steel Staples, Weck Closure Systems™, 1998, 220000723 Rev. 00, REF 528135, U.S. Patents (see above) 4,662,555 and 5,038,991.

Color Photo, Right Side View of Product in Packaging, Weck Visistat® Disposable Stapler with 35 Regular Staples, 5.7 mm×3.9 mm Stainless Steel Staples, Weck Closure Systems™, 1998, 220000723 Rev. 00, REF 528135, U.S. Patents (see above) 4,662,555 and 5,038,991.

Color Photo, Back of Packaging, Weck Visistat® Disposable Stapler with 35 Regular Staples, 5.7 mm×3.9 mm Stainless Steel Staples, Weck Closure Systems™, 1998, 220000723 Rev. 00, REF 528135, U.S. Patents (see above) 4,662,555 and 5,038,991.

Photocopy of Back of Packaging for TT.

Order Code 8886803512, APPOSE*ULC 35 Regular Skin Stapler; Order Code 8886803712, APPOSE*ULC 35 Wide Skin Stapler; http://www.autosuture.com, a Division of Tyco Healthcare Group LP, Skin Stapling Products, 1 page + home page (see above AA, BB, CC, DD); ©2002.

Order Code 055002, CONCORDE*-50W Disposable Skin Stapler; http://www.autosuture.com, a Division of Tyco Healthcare Group LP, Skin Stapling Products, 1 page + home page; ©2002.

Order Code 059035, Multifire Premium*-35 Skin Stapler; Order Code 059037, Multifire Premium*-35W; http://www.autosuture.com, a Division of Tyco Healthcare Group LP, Skin Stapling Products, 1 page + home page; ©2002.

Order Code 054873, ROYAL*-35 Disposable Skin Stapler; Order Code 054887, ROYAL*-35W Skin Stapler; http://www.autosuture.com, a Division of Tyco Healthcare Group LP, Skin Stapling Products, 1 page + home page (see above EE, FF, GG, HH); ©2002.

Order Code 054006, SIGNET*-35W Disposable Skin Stapler; http://www.autosuture.com, a Division of Tyco Healthcare Group LP, Skin Stapling Products, 1 page + home page; ©2002.

Excerpt from Kendall Online Catalogs, a division of TYCO Healthcare Group LP, Veterinary Surgical Products Catalog, Skin Stapling Products Regarding Multifire Premium Disposable Skin Staplers, Royal Disposable Skin Staplers and APPOSE Disposable Skin Staplers, 3 pages (see above AA-DD, EE-HH, WW); ©2002.

General information regarding Johnson & Johnson Gateway PROXIMATE Skin Staplers: Proximate RH, Proximate PX, Proximate Plus MD; http://www.jnjgateway.com, General Surgery, Mechanical Wound Closure, Skin Staplers, 3 pages; © 2000-2002.

Essential product information regarding Proximate Skin Stapler and Proximate Plus MD; http://www.jnjgateway.com, 2 pages; © 2000-2002.

Features and benefits regarding Proximate RH Skin Staplers, Proximate PX Skin Staplers, Proximate Plus MD Skin Staplers, http://www.jnjgateway.com, 3 pages; © 2000-2002.

Related information regarding Proximate Plus MD Skin Stapler, http://www.jnjgateway.com, 2 pages; © 2000-2002.

Device Description and Surgical technique regarding Proximate Plus MD Skin Stapler, http://www.jnjgateway.com, 3 pages; © 200-2002.

Related information regarding Proximate PX Skin Stapler, http://www.jnjgateway.com, 2 pages; © 2000-2002.

Related information regarding Proximate RH Skin Stapler, http://www.jnjgateway.com, 2 pages; © 2000-2002.

Device Description and Surgical technique regarding Proximate RH Skin Stapler, http://www.jnjgateway.com, 3 pages; © 2000-2002.

Features and benefits of Weck Visistat® Disposable Stapler, Weck Closure Systems™; http://www.weckclosure.com, 1 page, (see above QQ-TT); ©2000.

Production information regarding 3M™ Precise™ Vista Disposable Skin Stapler 3995; http://www.3M.com, 3M A-Z Product Index, S Index, 3 pages (see above II-LL); © 1999-2002.

Production information regarding 3M™ Precise™ PGX Disposable Skin Stapler PGX-35W; http://www.3M.com, 3M A-Z Product Index, S Index, 3 pages; © 1999-2002.

General production information regarding 3M™ Precise™ Multi-Shot Disposable Skin Stapler System; http://www.3M.com, 3M A-Z Product Index, S Index, 3 pages; © 1999-2002.

Production information regarding 3M™ Precise™ Multi-Shot Disposable Skin Stapler DS-5; 5 Staples (Arcuate-Style); http://www.3M.com, 3M A-Z Product Index, S Index, 2 pages; © 1999-2002.

Production information regarding 3M™ Precise™ Multi-Shot Disposable Skin Stapler DS-15; 15 Staples (Arcuate-Style); http://www.3M.com, 3M A-Z Product Index, S Index, 2 pages; © 1999-2002.

Production information regarding 3M™ Precise™ Multi-Shot Disposable Skin Stapler DS-25; 25 Staples (Arcuate-Style); http://www.3M.com, 3M A-Z Product Index, S Index, 2 pages; © 1999-2002.

Production information regarding 3M™ Precise™ Multi-Shot Disposable Skin Stapler MS-5; 5 Staples (Box-Style); http://www.3M.com, 3M A-Z Product Index, S Index, 2 pages; © 1999-2002.

Production information regarding 3M™ Precise™ Multi-Shot Disposable Skin Stapler MS-15; 15 Staples (Box-Style); http://www.3M.com, 3M A-Z Product Index, S Index, 2 pages; © 1999-2002.

Production information regarding 3M™ Precise™ Multi-Shot Disposable Skin Stapler MS-25; 25 Staples (Box-Style); http://www.3M.com, 3M A-Z Product Index, S Index, 2 pages (see above MM-PP); © 1999-2002.

Production information regarding 3M™ Precise™ Multi-Shot Disposable Skin Stapler MS-35; 35 Staples (Box-Style); http://www.3M.com, 3M A-Z Product Index, S Index, 2 pages; © 1999-2002.

Production information regarding 3M™ Precise™ Multi-Shot Disposable Skin Stapler RSH-100; http://www.3M.com, 3M A-Z Product Index, S Index, 2 pages; © 1999-2002.

Catalog information regarding 3M™ Precise™ Multi-Shot Disposable Skin Stapler System; http://www.3M.com, 3M A-Z Product Index, S Index, 3 pages; © 1999-2002; Faxable Document 72640; Apr. 2002.

Frequently Asked Questions for 3M™ Multi-Shot Disposable Skin Stapler System; http://www.3M.com, 3M A-Z Product Index, S Index, 1 page.

Delphion inventor, assignee patent search results for "Richard-Allan Medical"; http://www.delphion.com; 2 pages, searched and printed on Jan. 27, 2003.

Delphion inventor, assignee patent search results for "conmed"; http://www.delphion.com; 10 pages, searched and printed on Jan. 27, 2003.

Delphion search results for "((skin or surgical) and staple)" patents ; http://www.delphion.com; 17 pages, searched and printed on Jan. 27, 2003.

Delphion inventor, assignee patent search results for "Imagyn"; http://www.delphion.com; 2 pages, searched and printed on Jan. 27, 2003.

Production information regarding Sureline Skin Stapler™; http://www.designstandards.com; 3 pages, first publication unknown, printed on Jan. 27, 2003.

* cited by examiner

SURGICAL STAPLING DEVICE

CROSS-REFERENCE TO RELATED APPLICATIONS

This application is a continuation-in-part of U.S. application Ser. No. 10/156,716 filed on May 28, 2002, now abandoned which is hereby incorporated by reference in its entirety for all purposes.

STATEMENTS REGARDING FEDERALLY SPONSORED RESEARCH OR DEVELOPMENT

Not Applicable

REFERENCE TO A MICROFICHE APPENDIX

Not Applicable

BACKGROUND OF THE INVENTION

1. Field of the Invention

The present invention relates to health care devices comprising medical and veterinary devices, and more particularly to devices useful in suturing or closing wounds or incisions.

2. Description of the Related Art

The use of surgical staples in the health care field, comprising both the medical and veterinary fields, to close wounds and incisions has begun to, in many contexts, replace conventional suture ligature.

Surgical skin stapling has been found to be desirable in that it requires less skill of the health care clinician than conventional suture ligature. In addition, removal of staples is faster and easier than suture ligature. As in most fields, simplicity in wound and incision closure decreases the possibility of error, an accomplishment of particular importance in the health care field. Surgical stapling also provides better post-surgery aesthetic appearance than does conventional suture ligature and needle wound closure. Further still, postoperative infection is reduced in the use of skin stapling over suture ligature.

Because surgical stapling takes less time than conventional suture ligature, surgical stapling is economically advantageous. Both implanting and removing surgical staples is easier than placing and removing conventional sutures. It is, for example, estimated that the typical surgical stapling operation takes approximately 10% of the time of a conventional ligature placement. Thus, a significant time savings is involved in using surgical staples for wound and incision closure.

However, not all clinicians are able to take advantage of stapling technology because available surgical stapling devices are expensive. For example, clinicians who work in low-income regions or without insurance support, are often unable to afford currently available surgical staple devices and supplies. However, clinicians and their patients who can afford stapling devices end up benefiting economically in the long run.

While advantageous in the respects discussed, current surgical stapling devices present certain limitations. First, surgical stapling devices without a removable cartridge are designed so that the entire stapling device is discarded after all staples have been used. Such stapling devices are not economically advantageous in the long run. Also, because all parts of such a stapling device are disposed of after the staples are used, the quality of the parts must be sacrificed to keep costs down. However, if premium quality components are used, disposing of these parts each time the staples are used raises the cost of using the stapling device.

Current surgical stapling devices which do use a replaceable staple cartridge minimize the waste of many functional components of the stapling device. This recycling of parts for reuse is economically advantageous. However, current surgical stapling devices employing a replaceable cartridge do not allow for reuse of both a staple former and an anvil. Some of the staple cartridges currently in use include both a staple former and an anvil as an integral part of the replaceable cartridge, and all cartridges include at least an anvil or a staple former. By including an anvil and/or a staple former as an integral part of a replaceable cartridge, these components are disposed of with the staple cartridge. Reducing the disposal of functional parts is economically advantageous. Therefore, it is desirable to have a surgical stapling device in which a stapling cartridge does not include either a staple former or an anvil as an integral component of the staple cartridge.

Current surgical staple devices generally provide a feeder shoe to urge a plurality of staples toward the staple-forming or exiting end of the stapling device. A limitation in such feeder shoes and urging mechanisms is that staples are allowed to jam on the sliding surface as the staples move toward the staple-forming or exiting end of the stapling device.

Such staple jams can be at least inconvenient to clinicians who temporarily cannot utilize the stapling device. A limitation in the feeder shoes and urging mechanisms which can lead to staple jams is that while all such feeder shoes contact at least a part of one of the staples, and some feeder shoes contact much of one side of a staple, when a staple slips, the staple can be lodged in spaces either between the staple stack containing a plurality of staples and the track upon which the plurality of staples slide, within other spaces existing within the feeder shoe itself, or between the feeder shoe and the track upon which the staple stack slides. It is therefore desirable to have a staple housing, such as a staple cartridge, in which the outer surfaces of a feeder shoe are continuous with the staple housing and in which the feeder shoe acts as a traveling blocking surface against a fixed blocking surface.

Another limitation of current feeder shoes is that if such feeder shoes are extended completely to the end of the staple cartridge, as when all staples in the staple cartridge have been used so that no staples remain in the staple cartridge, forcing the staple former on the feeder shoe can damage these parts. It is therefore desirable to avoid this force on the feeder shoe and staple former.

Finally, a limitation of current surgical stapling devices is that staples are implanted substantially orthogonal to the skin surface. By inserting staples at an angle of between about 10°–45° relative to the skin surface and then tilting the staple so that the staple is ultimately positioned substantially orthogonal to the skin surface, greater resulting anastomosis can be obtained as the skin grows together. This greater anastomosis allows for shorter healing time. Thus, it is desirable to have a stapling device in which a staple can be inserted at an angle of about 10°–45° relative to the skin, the staple subsequently rotated to a final orientation being substantially orthogonal to the skin's surface.

BRIEF SUMMARY OF THE INVENTION

According to the invention, a surgical stapling device has a body member having a staple cartridge recess, a trigger member movably positioned with the body member, a staple former positioned with the body member movably positioned with the trigger member, a staple cartridge having a staple, the staple cartridge removably positioned with the staple cartridge recess and an anvil member positioned with the body member for transforming the staple from a pre-implantation configuration to a post-implantation configuration upon movement of the trigger member from an at-rest position to a staple-forming position. The preferred embodiment also includes a body member having an aligning surface for implantation of the staple at an insertion angle relative to the skin surface of between about 10° and about 45°.

The surgical staple cartridge includes a housing member having a staple-forming end, a plurality of staples having a lead staple movably positioned in the housing member and a first opening in the staple-forming end of the housing member to allow access to the lead staple and a second opening in the staple-forming end of the housing member to allow the lead staple to move therethrough. The staple cartridge preferably contains a feeder shoe for urging the plurality of staples toward the staple-forming end of the housing member. To prevent staple jamming, the staple cartridge also preferably contains a fixed blocking surface on the housing member and a traveling blocking surface on the feeder shoe. The traveling blocking surface is sized so that the feeder shoe moves along the fixed blocking surface of the housing member while blocking the staple. The staple cartridge also preferably includes a flexible arm extending from the housing member and moving between a memory position and a flexed position outwardly from the memory position for a snap fit of the staple cartridge to the stapling device. Additionally, the feeder shoe is angled to prevent damage to the staple former and feeder shoe when the trigger member is squeezed when no staples remain in the staple cartridge.

BRIEF DESCRIPTION OF THE SEVERAL VIEWS OF THE DRAWINGS

Various objects and advantages of this invention will become apparent and more readily appreciated from the following description of the presently preferred exemplary embodiments, taken in conjunction with the accompanying drawings, of which.

DETAILED DESCRIPTION OF THE INVENTION

Figure 1:
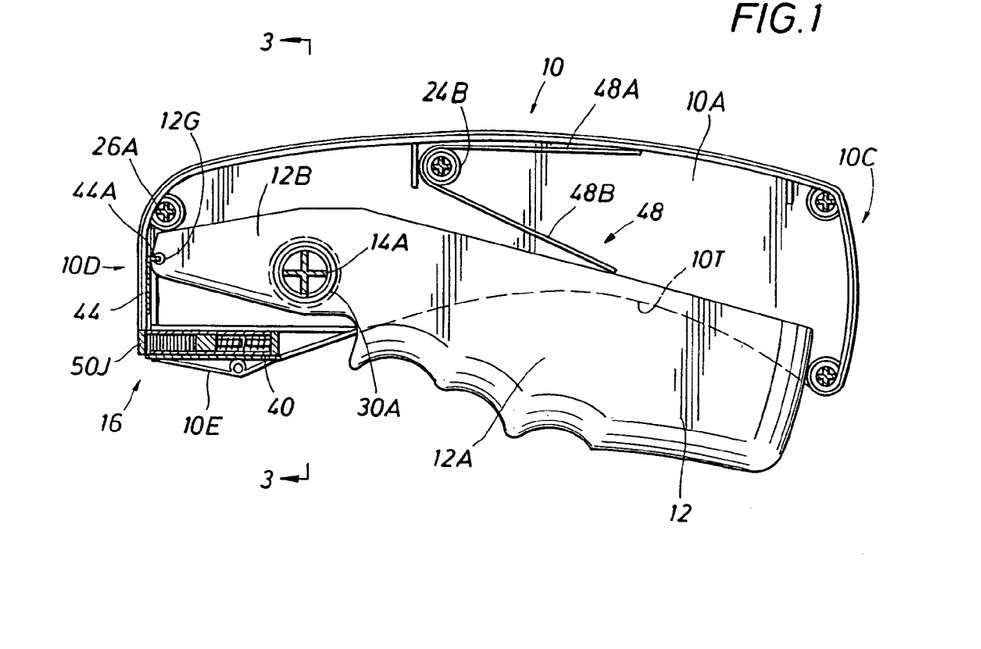
FIG. 1 is a side elevational view of the right body member half of the surgical stapling device of the present invention to better illustrate the trigger member in the at-rest position.
Figure 2:
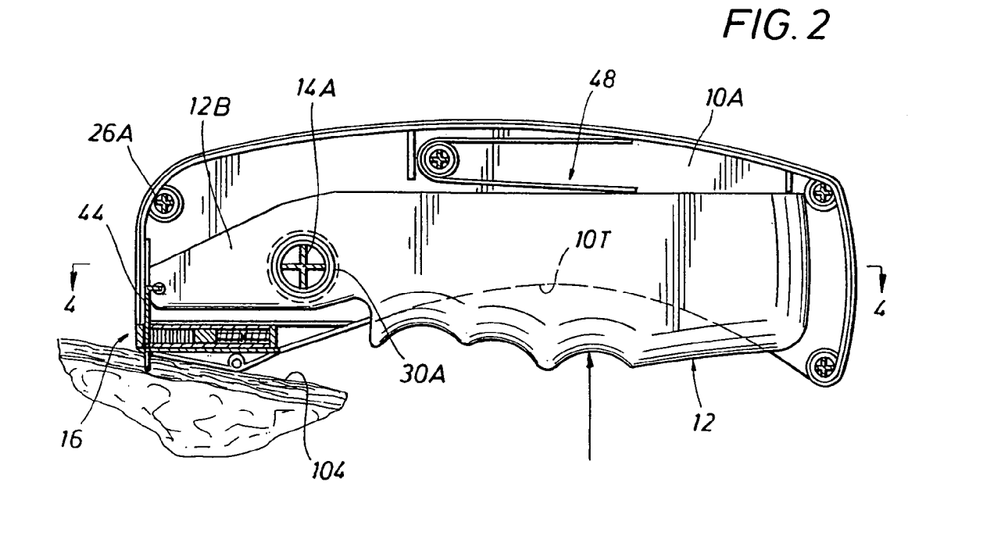
FIG. 2 is a side elevational view of the right body member half of the stapling device of the present invention to better illustrate the trigger member in the staple-forming position.
Figure 4:
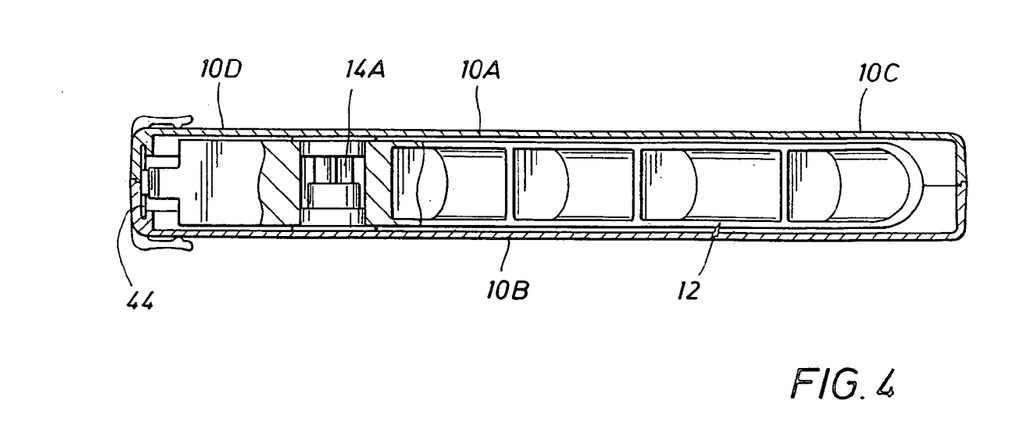
FIG. 4 is a cross sectional view taken along section line 4—4 of FIG. 2.
Figure 5:
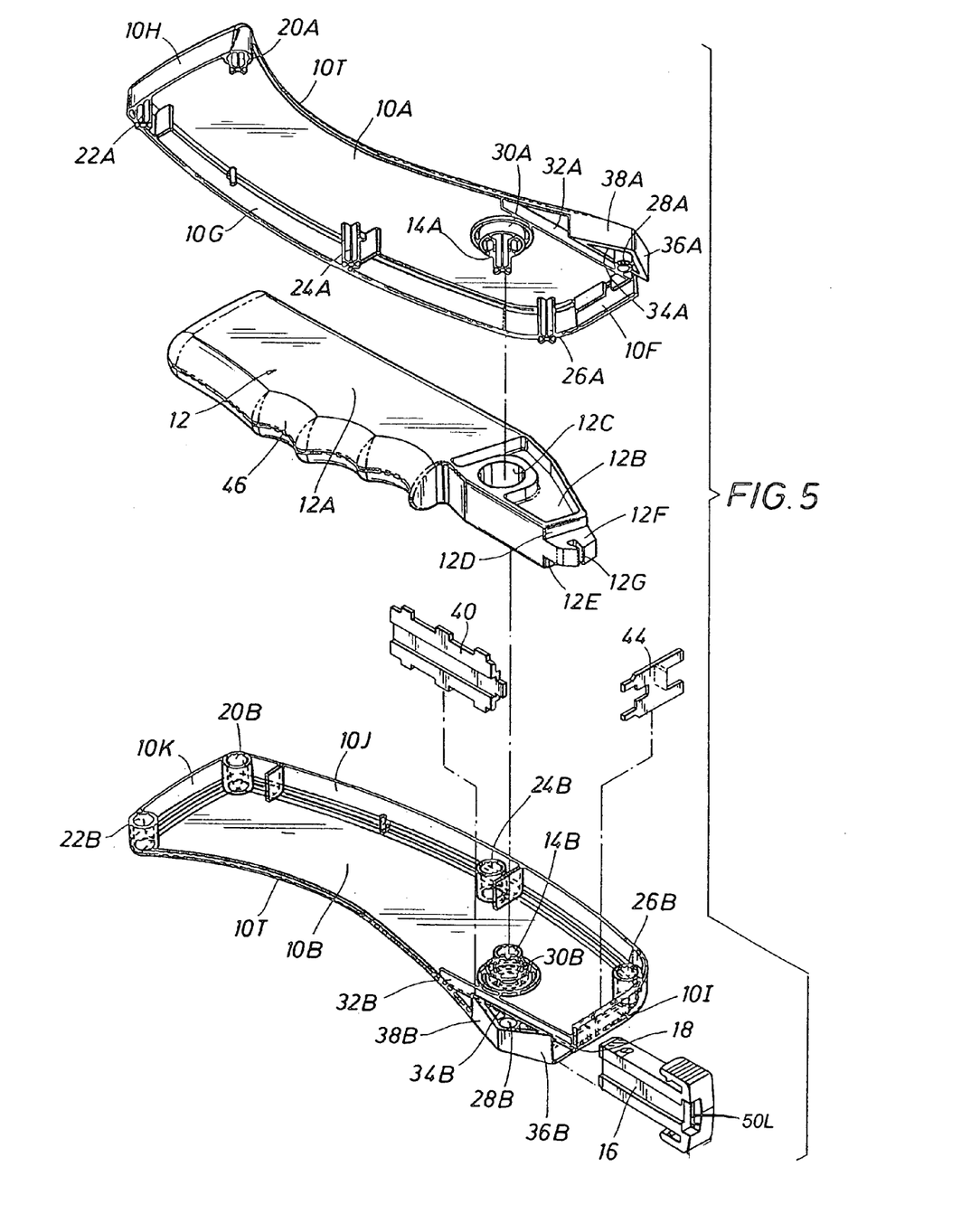
FIG. 5 is an exploded view of right and left body member halves to better illustrate the trigger member, anvil, staple cartridge and staple former.
Figure 6:
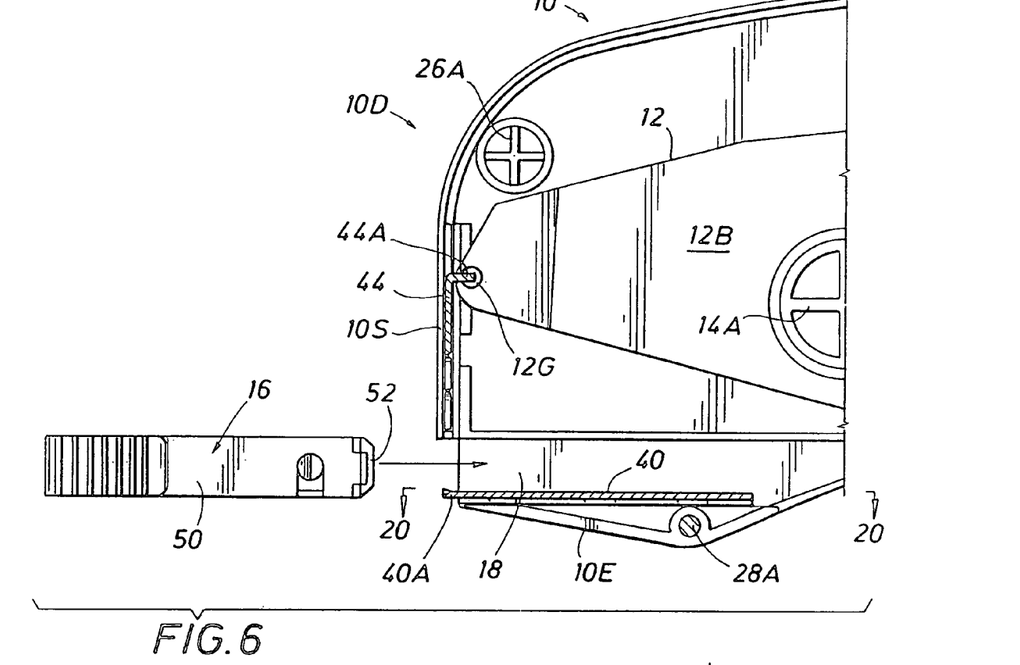
FIG. 6 is a fragmentary side elevational view of the right body member half of the stapling device of the present invention to better illustrate the insertion of the staple cartridge into the staple cartridge recess.
Figure 7:
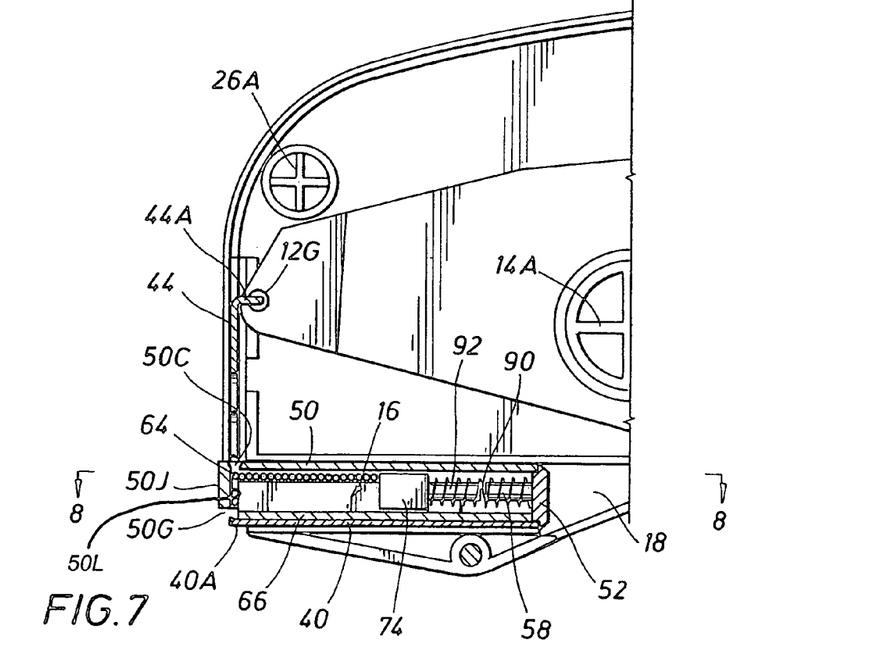
FIG. 7 is a fragmentary side elevational view of the right body member half of the stapling device of the present invention to better illustrate the inserted staple cartridge relative to the staple former.

As shown in FIG. 1, the surgical stapling device of the present invention comprises a body member, generally indicated as 10, and a trigger member 12 movably positioned with the body member 10. As best shown in FIG. 5, the trigger member 12 is pivotally movable about a trigger pivot opening 12C. Preferably, the body member 10 comprises a right body member half 10A and a left body member half 10B. The body halves are assembled in mated relationship, as best shown in FIG. 5. Also as shown in FIG. 5, the trigger pivot opening 12C is received about right trigger pivot male member 14A and a left trigger pivot female member 14B that are interengaged in a mated relationship. As best shown in FIG. 4, the body member 10 has a rearward portion 10C constituting a handle portion and a forward portion 10D. As best shown in FIGS. 6 and 7, a staple cartridge 16 is located within a staple cartridge recess 18 in the forward portion 10D. Returning to FIG. 1, the rearward or handle portion 10C of body member 10 is used at an angle related to the forward portion 10D so that the instrument can be properly positioned in the hand of a clinician. An aligning surface 10E of the body member 10 facilitates application of staples at a consistent angle relative to the skin surface. As shown in FIGS. 1 and 2, this insertion angle is about 10°. However, other embodiments consistent with the present disclosure provide for aligning surfaces corresponding to insertion angles of about 10° to about 45° relative to the skin surface. The desired angle will be determined by the height of the user of the stapling device. For example, a shorter person would desire a smaller angle.

Turning again to FIG. 5, the right body member half 10A has edge portions 10F, 10G and 10H adapted to engage and be joined to edge portions 10I, 10J and 10K, respectively, of left body member half 10B. As can be seen from FIG. 3, right and left body member halves 10A and 10B are oppositely stepped so as to have an overlapping mating relationship when abutted. As shown in FIG. 5, right body member half 10A has five male members 20A, 22A, 24A, 26A and 28A formed thereon. The left body member half 10B has five corresponding female members 20B, 22B, 24B, 26B and 28B thereon. When the body member halves 10A and 10B are joined together, male members 20A, 22A, 24A, 26A and 28A are received within female members 20B, 22B, 24B, 26B and 28B, respectively, with a snap fit. The pivot members 14A and 14B are simultaneously snap fitted when the halves are joined.

The body member halves 10A and 10B in the embodiment illustrated are molded of appropriate plastic material suitable for use in a surgical environment and capable of withstanding sterilization by any one or more of the standard sterilization procedures well known in the art. Preferably, a polycarbonate or like thermoplastic resin is used. Once the internal components of the surgical stapling device (to be described hereinafter) have been assembled in one of the body halves, the body halves are joined together. The halves are joined preferably by an arbor press, but may be joined by any similar joining means known in the art. In addition to the frictional engagement of female members 20B, 22B, 24B, 26B and 28B with male members 20A, 22A, 24A, 26A and 28A, the mated edges 10F, 10G and 10H and 10I, 10J and 10K may be permanently bonded by gluing, welding or the like. It will be understood by one skilled in the art that if the instrument of the present invention is to be non-disposable and reusable, body member halves 10A and 10B can be fabricated of stainless steel or other appropriate material suitable for use in a surgical environment and capable of being sterilized. Under such circumstances, the body member halves 10A and 10B will be held together by removable fastening means such as screws or the like.

Remaining at FIG. 5, right body member half 10A has an annular flange 30A, a rectilinear flange 32A, and three triangularly conjoined rectilinear flanges 34A, 36A and 38A. The left body member half 10B has an annular flange 30B, equivalent to annular flange 30A, a rectilinear flange 32B, equivalent to rectilinear flange 32A, and three triangularly conjoined rectilinear flanges 34B, 36B and 38B equivalent to flanges 34A, 36A and 38A, respectively. When the body halves are assembled, annular flanges 30A and 30B are opposed and coaxial, and flanges 32A, 34A, 36A and 38A are in opposed relationship to flanges 32B, 34B, 36B and 38B, respectively.

Figure 20:
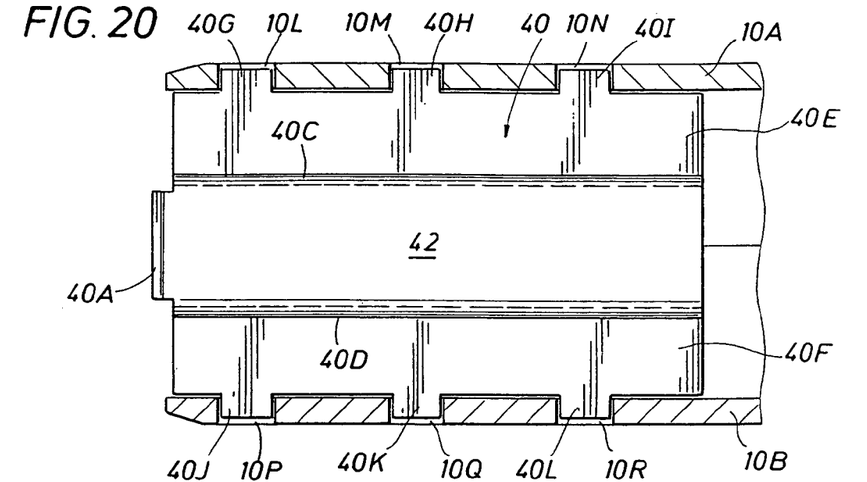
FIG. 20 is a fragmentary top elevational view of the anvil of the housing member of the present invention.

Reference is now made to FIGS. 1 and 2, which illustrate the right body member half 10A of the stapling device with the internal elements mounted therein. Turning first to the forward portion 10D of the stapling device, there is housed therein an anvil member 40. The anvil member 40 is best seen in FIG. 20. The anvil member 40 is preferably formed of an appropriate metal for use in a surgical environment, such as stainless steel or the like. The anvil member 40 has a longitudinally extending raised central portion 42. At its forwardmost end, the raised central portion 42 has an extended tab 40A comprising an integral one-piece part of the raised central portion 42 and lying at a slight angle thereto. The tab 40A constitutes an anvil and the upper surface 40B of tab 40A constitutes an anvil surface which is coextensive with the upper surface of the raised central portion 42.

Figure 3:
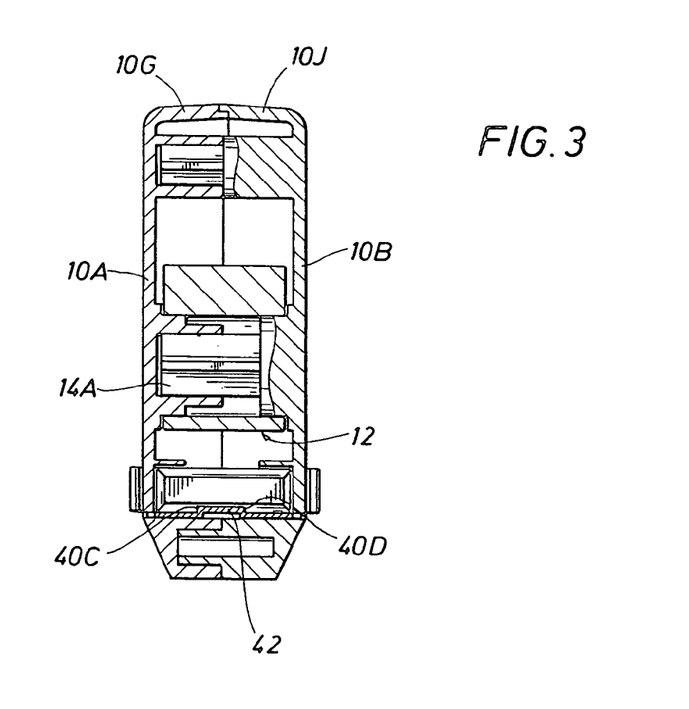
FIG. 3 is a cross sectional view taken along section line 3—3 of FIG. 1.

Remaining at FIG. 20, the raised central portion 42 of anvil member 40 has lateral edges which terminate in downwardly depending portions 40C and 40D (see also FIG. 3). The downwardly depending portions 40C and 40D, in turn, terminate in laterally extending flanges 40E and 40F. Flange 40E is provided with three extensions 40G, 40H and 40I. Similarly, flange 40F is provided with three extensions 40J, 40K and 40L. The right body member half 10A (see FIG. 20) has three recesses 10L, 10M and 10N formed therein. In similar fashion, the left body member half 10B has three recesses 10P, 10Q and 10R formed therein. When the body member halves 10A and 10B are joined together with the anvil member 40 properly located therebetween, the extensions 40Q 40H and 40I of flange 40E will be received within recesses 10L, 10M and 10N of right body member half 10A, respectively. Similarly, the extensions 40J, 40K and 40L of flange 40F will be received within recesses 10P, 10Q and 10R of left body member half 10B. In this way the anvil member 40 is properly located and locked within the body halves. It is also evident from FIG. 3 that anvil member flanges 40E and 40F rest upon the bottom portions of right and left body halves 10A and 10B.

Figure 9:
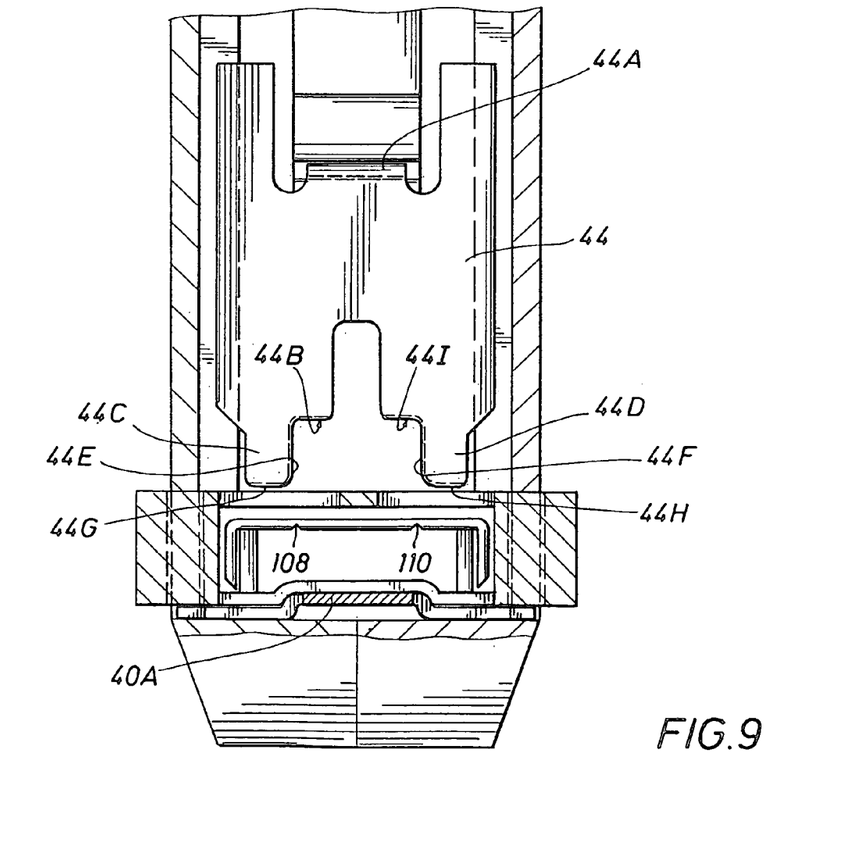
FIG. 9 is a fragmentary cross sectional view, taken along section line 9—9 of FIG. 8.

Turning now to FIGS. 6, 7 and 9, mounted within the forward portion 10D of the stapling device body member 10 there is a staple former 44. As can be best seen in FIG. 9, the staple former 44 comprises a substantially planar, substantially rectangular element preferably made of metal suitable for use in a surgical environment, such as stainless steel or the like. The staple former 44 is provided with a tab 44A rearwardly extending from the staple former 44. The purpose of the tab 44A will be described hereinafter.

At its lowermost end the staple former 44 has staple-forming notches 44B and 44I formed therein, as shown in FIG. 9. To the right side of staple-forming notch 44B and the left side of staple-forming notch 44I are two prongs 44C and 44D of staple former 44. At the lowermost corners 44E and 44F of the notches, the staple former 44 may be slightly rounded, as shown in FIG. 9. This assists in bending the staples, as will be described hereinafter. The lowermost edges 44G and 44H and the adjacent rounded corners 44E and 44F (the first portions of the staple former 44 to contact the crown of a staple) may be slightly grooved to assure that the staple being formed by the staple former 44 is properly aligned during the initial phase of the staple-forming procedure.

As is most clearly shown in FIG. 6, the staple former 44 is located in abutment with the front inside surface 10S of the forward portion 10D of the body member 10. The staple former 44 is slidable along inside surface 10S between a first retracted or at-rest position illustrated in FIGS. 1, 6, 7 and 9, and a second extended or staple-forming position shown in FIGS. 2 and 11. Female member 26B, which receives male member 26A as shown in FIG. 5, serves as a stop for nose portion 12B of trigger member 12 so as to determine a first retracted or at-rest position of staple former 44.

To shift the staple former 44 between its first and second positions, as illustrated in FIGS. 1 and 2, the trigger member 12 is actuated. The trigger member 12 (best shown in FIG. 5) lends itself well to be molded of an appropriate plastic material for use in a surgical environment and comprises a handle portion 12A and a nose portion 12B. The handle portion 12A is hollow and extends through an elongated opening created by edges 10T (see FIGS. 1, 2, and 5) in the body member 10. The lower edge portion of trigger member 12 is adapted to be grasped by the fingers of the clinician and, to this end, may be notched or serrated as at 46. The nose portion 12B of trigger member 12 is on the other side of trigger pivot opening 12C. The trigger pivot opening 12C is adapted to rotatively receive annular flange 30A of right body member half 10A and annular flange 30B of left body member half 10B.

As best shown in FIG. 5, the nose portion 12B of trigger member 12 terminates in surfaces 12D and 12E, flanking a central surface 12F. As best shown in FIGS. 6 and 7, the forward end of nose portion 12B comprises an attachment channel 12G which is adapted to receive rearwardly extending tab 44A of staple former 44. Thus, the nose portion 12B of trigger member 12 maintains the staple former 44 in abutment with the front inside surface 10S of the forward portion 10D of the body member 10.

As shown in FIGS. 6 and 7, the tab 44A is inserted into an attachment channel 12G at the forwardmost tip of nose portion 12B of the trigger member 12. As shown in FIGS. 1 and 2, when handle portion 12A of the trigger member 12 is squeezed against the action of a leaf spring member, generally indicated at 48, the nose portion 12B of the trigger member 12 pivots in a counterclockwise direction so that the attachment channel 12G and tab 44A contained therein moves downward toward the staple cartridge 16.

As is best shown in FIGS. 1 and 2, leaf spring member 48 is mounted in the body member 10. The leaf spring member 48 is substantially V-shaped, having a first leg 48A bearing against the upper inside surface of body member 10 and a second leg 48B lying along the upper surface of trigger member 12. Both legs move about female member 24B. Leaf spring member 48 will maintain trigger member 12 in its at-rest position, as illustrated in FIG. 1. This, in turn, assures that staple former 44 is in its first retracted or at-rest position. Upon squeezing trigger member 12 to cause it to pivot in a counterclockwise position (as viewed in FIGS. 1 and 2), the nose portion 12B thereof will cause staple former 44 to shift to its second extended or staple-forming position, as shown in FIG. 2.

Figure 8:
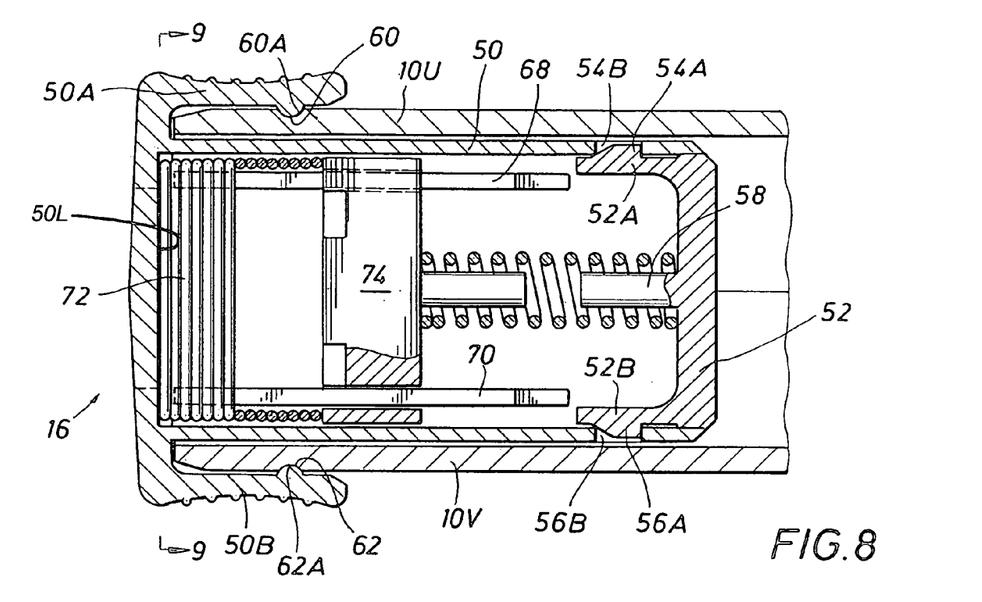
FIG. 8 is an enlarged fragmentary cross sectional view, taken along section line 8—8 of FIG. 7.
Figures 15, 16:
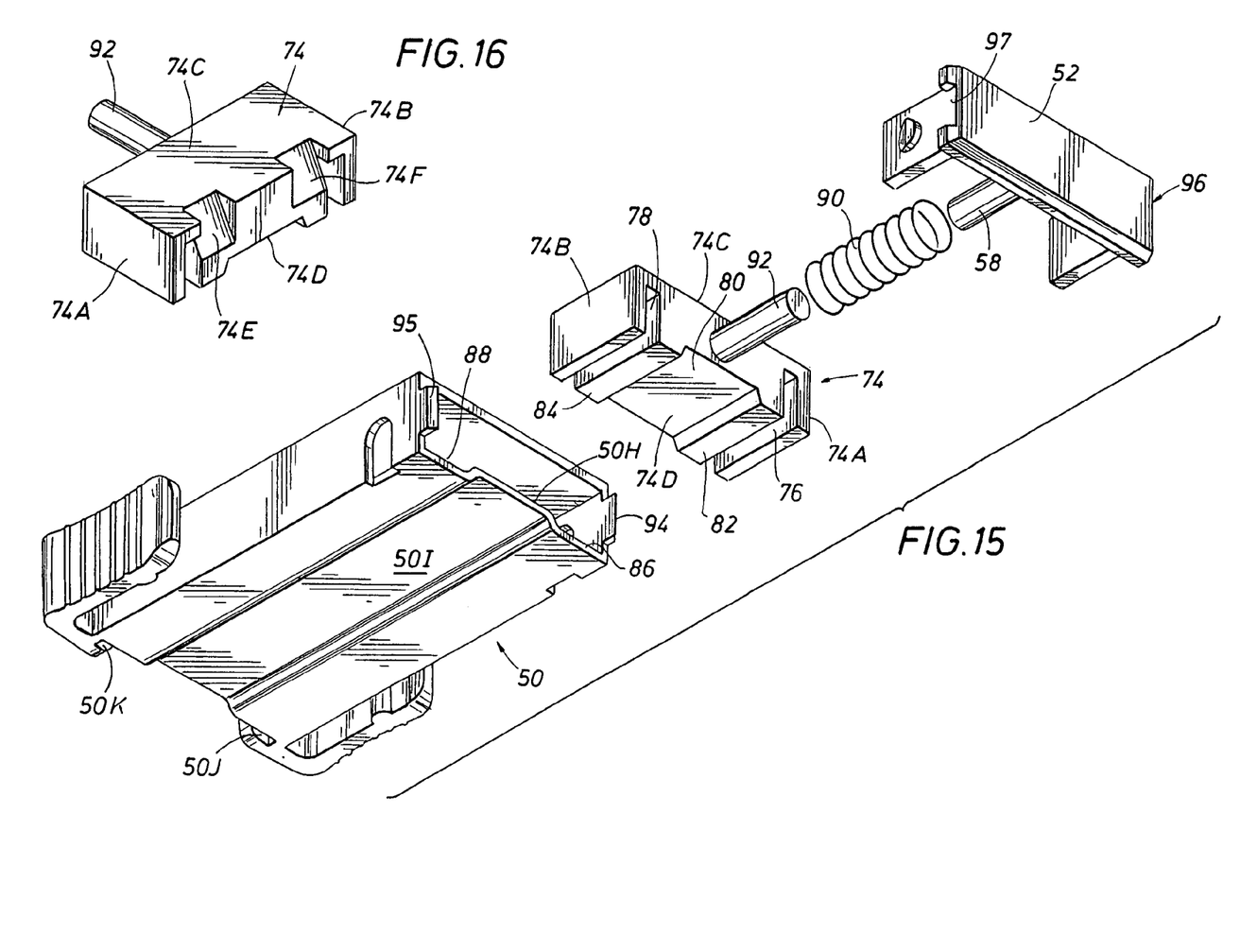
FIG. 15 is a perspective exploded view of the staple cartridge of the present invention.
FIG. 16 is a perspective view of the feeder shoe of the present invention.

As best shown in FIGS. 5–8, the staple cartridge 16 is removably inserted into the staple cartridge recess 18. As seen in FIGS. 8 and 15, the staple cartridge 16 comprises a housing member 50. The housing member 50 is preferably constructed from an appropriate plastic material for use in a surgical environment, but may be made from any material appropriate for housing staples, including metals.

A cap 52 is attached to the rear end of the housing member 50. The cap 52 is affixed to the housing member 50 by snaps, generally indicated at 54A and 56A. Snap 54A is removably affixed to snap receptacle 54B on the housing member 50. Snap 56A is removably affixed to snap receptacle 56B on the housing-member 50. Snaps 54A and 56A are located on flexible arms 52A and 52B, respectively, of the cap 52. As best seen in FIG. 8, the arms 52A and 52B are biased outward toward a memory position resting against housing member 50. The snaps are preferably bonded by permanent bonding means known in the art such as ultrasonic bonding, gluing, welding or any bonding method which can permanently affix the cap 52 to the housing member 50. It is intended that cap 52 upon being affixed is not removable or replaceable and that staple cartridge 16 is not reusable.

As shown in FIG. 8, the cap 52 also comprises a pusher rod 58 centrally attached to the cap 52 of housing member 50. Housing member 50 also includes flexible arms 50A and 50B, by which the housing member 50 is attached to the body member 10 of the stapling device by snaps, generally indicated as 60 and 62, respectively. Snap 60 is removably affixed to snap receptacle 60A on side 10U of body member 10 of the stapling device. Snap 62 is removably affixed to snap receptacle 62A on side 10V of body member 10 of the stapling device.

Snaps 60 and 62 are located on arms 50A and 50B, respectively, of the housing member 50. Arms 50A and 50B are biased inward toward a memory position against sides 10U and 10V of body member 10, as seen in FIG. 8, but both arms 50A and 50B may be flexed outward to insert and remove snaps 60 and 62.

Figure 17:
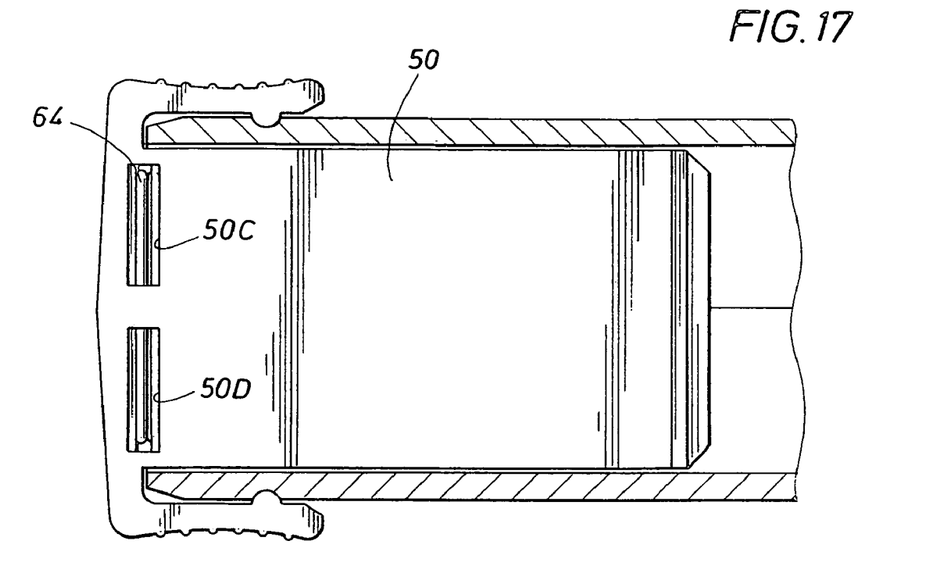
FIG. 17 is a fragmentary top elevational view of the staple cartridge of the present invention inserted into the stapling device.

As shown best in FIG. 17, housing member 50 comprises first openings 50C and 50D adjacent the front or staple-forming end 50L of housing member 50. First openings 50C and 50D are aligned vertically with lead staple 64, as shown in FIG. 7. First openings 50C and 50D allow staple former 44 to move into housing member 50 and to apply a force to lead staple 64. As shown in FIG. 17, angled surfaces assist in guiding prongs 44C and 44D of staple former 44 to lead staple 64.

Figure 18:
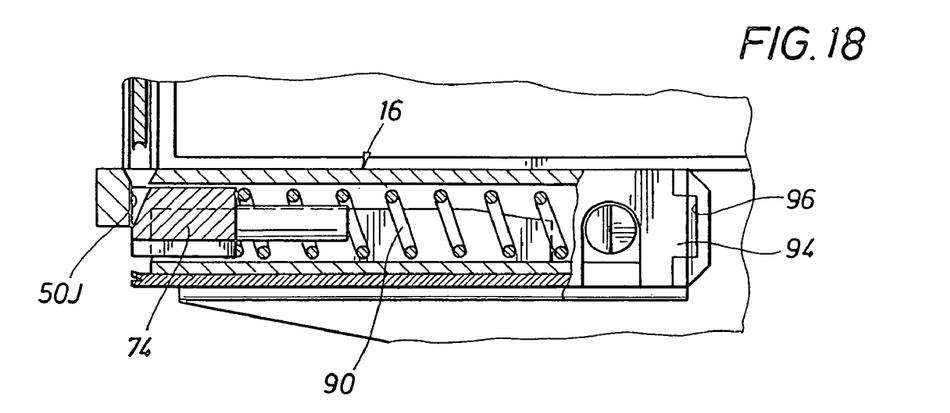
FIG. 18 is a fragmentary cross sectional view of the staple cartridge of the present invention inserted into the stapling device and with the staple former in the at-rest position.
Figure 19:
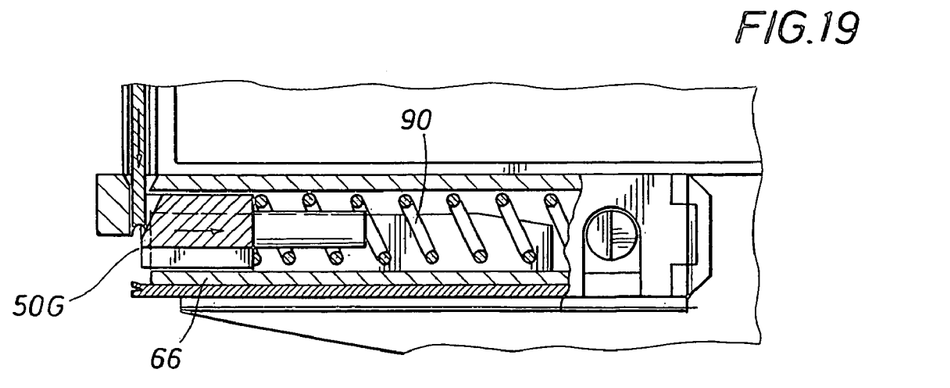
FIG. 19 is a fragmentary cross sectional view of the staple cartridge of the present invention with the staple former urging the feeder shoe away from the staple-forming end of the staple cartridge.

A second opening 50G in the staple-forming end 50L of housing member 50 is also aligned vertically with lead staple 64, as shown in FIGS. 6 and 7, as well as FIGS. 17–19. This second opening 50G is created by the ending of the bottom wall 66, as shown in FIG. 7. The second opening 50G allows lead staple 64 to move through the second opening 50G and strike anvil tab 40A upon the lead staple 64 being struck by staple former 44.

Figure 14:
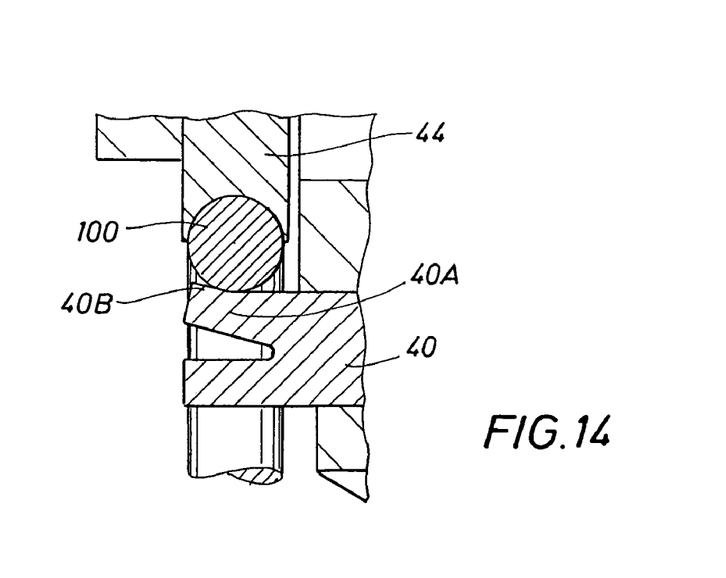
FIG. 14 is an enlarged cross sectional view taken along section line 14—14 of FIG. 11.

As best shown in FIGS. 7 and 8, the staples of the staple stack 72 are vertically oriented in the staple cartridge 16 relative to the movement of the staples along a substantially straight movement path through the staple cartridge 16. When a staple reaches the front or staple-forming end 50L of the staple cartridge 16, the staple is vertically aligned with the first openings 50C and 50D (FIG. 17) and second opening 50G (FIG. 19), as described above, thus those openings 50C, 50D, and 50G are also vertically oriented to the staple cartridge 16. Side 74D of the feeder shoe 74 (FIG. 15) is also parallel with the crown portion 100 (FIGS. 12 and 14) of the staples of the staple stack 72, as best shown in FIG. 8.

Figure 10:
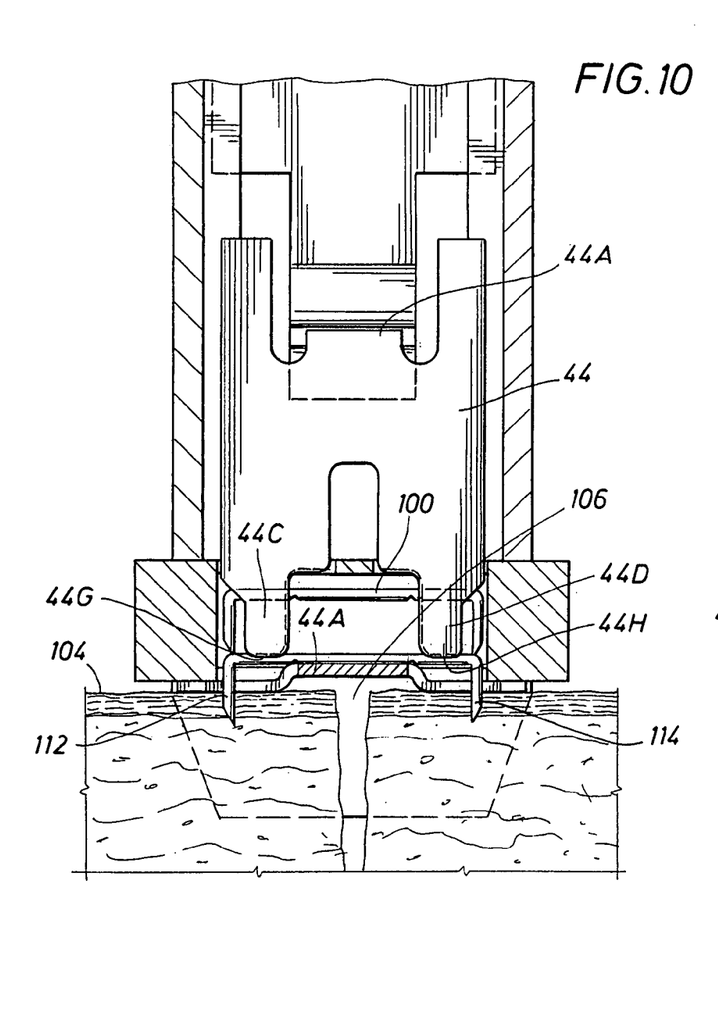
FIG. 10 is a fragmentary cross sectional view similar to FIG. 9, illustrating insertion by the surgical stapling device of the present invention of a pre-implantation configured staple into skin.

As best shown in FIG. 8, staple cartridge housing member 50 comprises staple feeder ramps 68 and 70 within housing member 50. The staple stack 72 containing a plurality of staples in a pre-implantation configuration (as seen in FIGS. 8–10) rests upon staple feeder ramps 68 and 70, and slides toward the fixed front or staple-forming end 50L of the staple cartridge 16 formed between frontal tabs 50J and 50K (FIG. 15), upon the staple feeder ramps 68 and 70 when urged by the feeder shoe 74. As best shown in FIGS. 15 and 16, feeder shoe 74 comprises feeder ramp grooves 76 and 78, through which staple feeder ramps 68 and 70 (see FIG. 8), respectively, insert, allowing feeder shoe 74 to slidably travel along staple feeder ramps 68 and 70 toward the front of staple cartridge 16.

As shown best in FIG. 15, feeder shoe 74 also comprises a groove 80. This groove 80 fits onto track 50H of the housing member 50, allowing the feeder shoe 74 to slidably travel along the upper surface of track 50H toward the front of staple cartridge 16 with guiding blocks 82 and 84 of feeder shoe 74 sliding along guiding block grooves 86 and 88 of housing member 50, respectively. The anvil member 40 rests against the bottom side of track 50H comprising groove 501, as shown in FIG. 15.

It will be apparent from FIGS. 15 and 16 that when feeder shoe 74 is slidably inserted into housing member 50, the feeder shoe 74 is fully configured with the housing member 50 such that both right and left sides 74A and 74B, respectively, as well as top and bottom sides 74C and 74D, respectively, are in continuity with all inside surfaces of housing member 50, so that staple feeder ramps 68 and 70, track 50H, frontal tabs 50J and 50K and the remaining inside surface of housing member 50 constitute a fixed blocking surface while feeder ramp grooves 76 and 78, guiding blocks 82 and 84, as well as the remaining outer surface of feeder shoe 74, including sides 74A, 74B, 74C and 74D constitute a traveling blocking surface. By reducing space between the outer surfaces of feeder shoe 74 and the inner surfaces of housing member 50, the possibility of staple jamming is decreased because the space into which a staple may lodge is reduced. Feeder shoe 74 additionally comprises a feeder rod 92. A spring 90 is positioned with feeder rod 92 that is received in pusher rod 58, as best shown in FIGS. 7, 8 and 15.

When cap 52 is affixed to housing member 50 using snaps 54A and 56A, as previously described, cap tabs 94 and 95 fit within cap tab inserts 96 and 97, as seen in FIGS. 15, 18 and 19. When cap 52 is so affixed, spring 90 exerts a force against feeder shoe 74, biasing the feeder shoe 74 toward the front or staple-forming end 50L of staple cartridge 16. As best seen in FIG. 8, the feeder shoe 74 moves toward the front or staple-forming end 50L of housing member 50, thus moving the staple stack 72 containing a plurality of staples toward the front or staple-forming end 50L as well.

Feeder shoe 74 additionally comprises angles 74E and 74F. As best shown in FIG. 16, the angles 74E and 74F each comprise a surface slanted away from vertical toward the pusher rod 58 at an angle of about 45°. The angles 74E and 74F move the feeder shoe 74 rearward toward the pusher rod 58 (toward the staple feeding or rear end) when the prongs 44C and 44D of the staple former 44 (see FIG. 9) strike the angles 74E and 74F, such as when there are no more staples in staple cartridge 16. Such movement prevents damage to the edges of the prongs 44C and 44D (see FIG. 9) of the staple former 44 when the trigger member 12 is squeezed when no staples remain in the staple cartridge 16. FIG. 18 shows a staple cartridge 16 with no staples therein, with feeder shoe 74 engaged with frontal tabs 50J and 50K of housing member 50. FIG. 15 best illustrates the frontal tabs 50J and 50K. FIG. 19 shows feeder shoe 74 moving rearward towards pusher rod 58 in response to a downward strike by staple former 44 when no staples remain in the staple cartridge 16.

Figure 11:
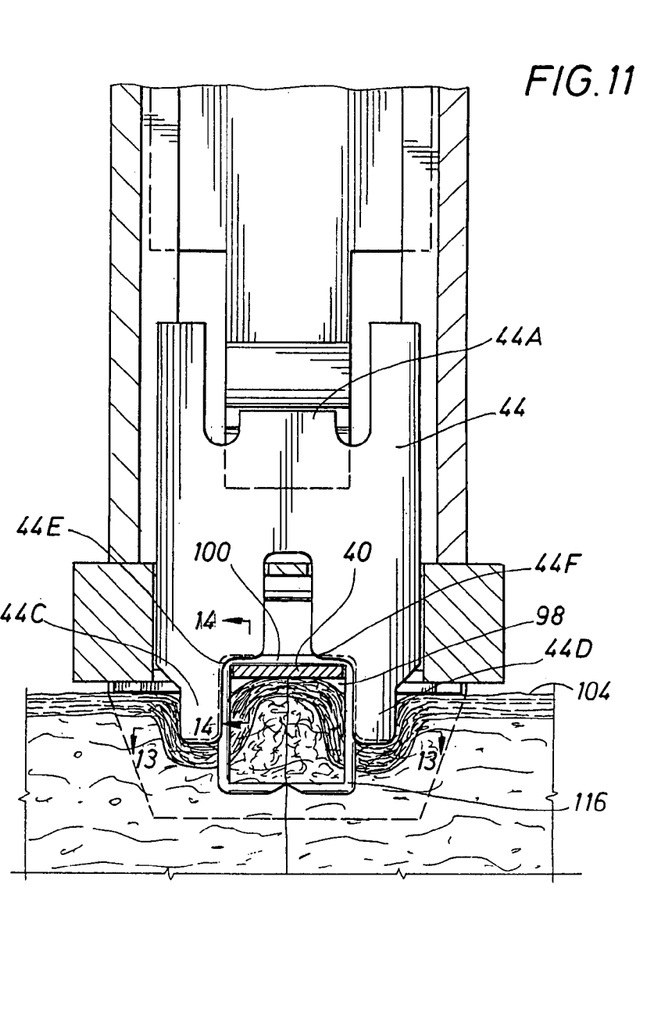
FIG. 11 is a fragmentary cross sectional view similar to FIGS. 9 and 10, illustrating insertion of a post-implantation configured staple in the skin.
Figure 12:
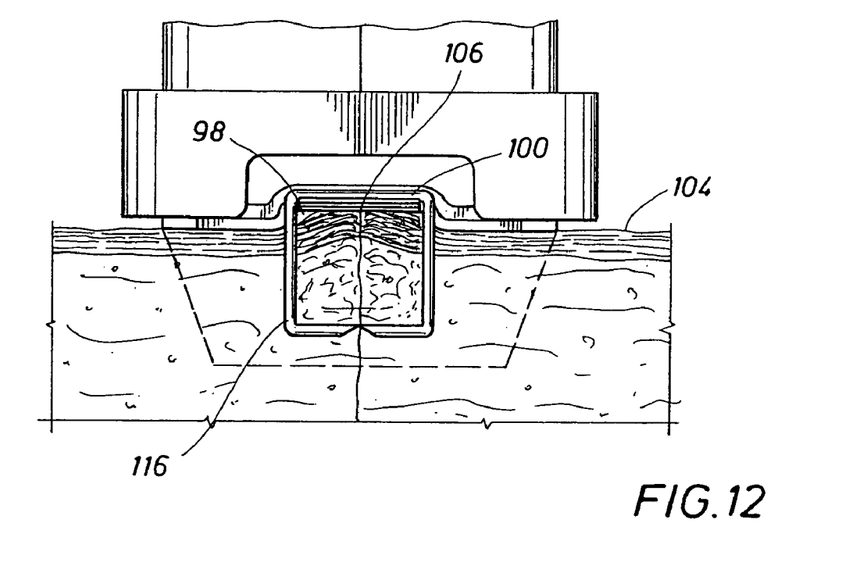
FIG. 12 is a fragmentary cross sectional view similar to FIGS. 9–11, illustrating a post-implantation configured staple in the skin.
Figure 13:
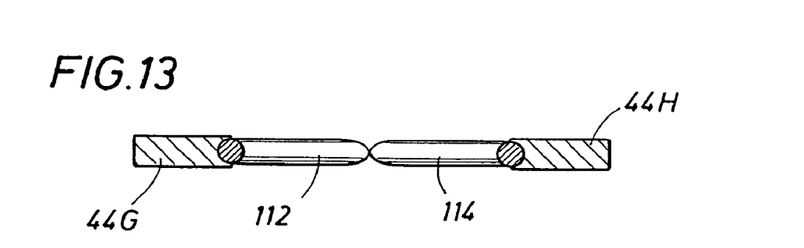
FIG. 13 is an enlarged cross sectional view taken along section line 13—13 of FIG. 11.
Figure 21:
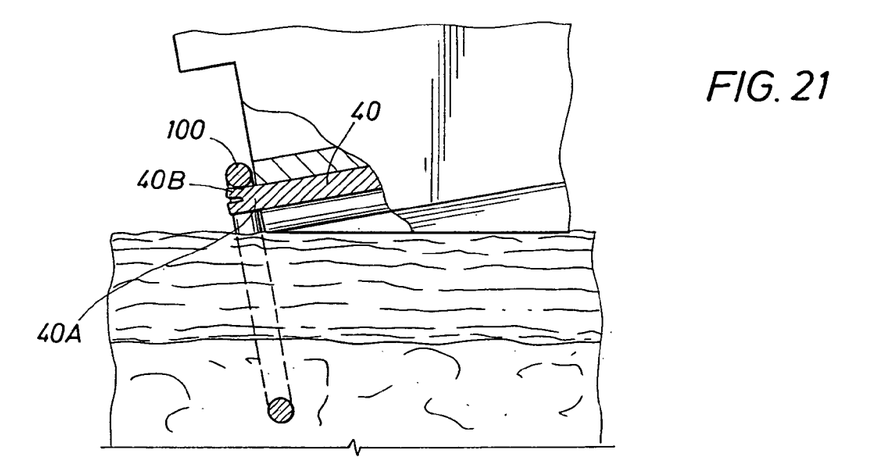
FIG. 21 is a fragmentary side elevational view of the stapling device of the present invention to better illustrate the relationship of the implanted staple and the anvil.
Figure 22:
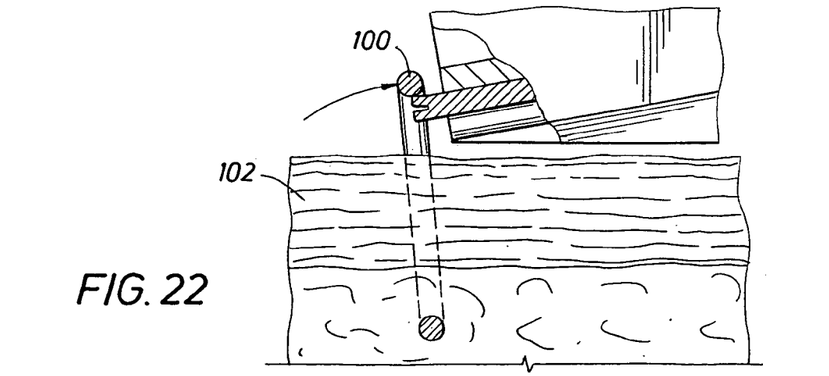
FIG. 22 is a fragmentary side elevational view of the stapling device of the present invention to better illustrate the relationship of the implanted staple and the anvil.

As described previously, staples are inserted into the skin surface at an insertion angle of about 10° from vertical, as best shown in FIG. 21. In order to bring the implanted staple to vertical, the upper surface 40B of anvil tab 40A is angled upward relative to the rest of the tab 40A. This provides frictional force sufficient to rotate the implanted staple towards vertical when the stapling device is moved rearwardly in the normal course of inserting multiple staples. When the staple is near vertical, the force of compressed skin pressing against the legs of the staple exceeds the frictional force exerted by the upper surface 40B of tab 40A on the crown of the staple, and the anvil 40 slides out from underneath the crown portion 100 of the staple. As the staple is brought to an angle near vertical as shown in FIG. 22, a crowning space 98, as shown in FIG. 11, is minimized. FIG. 11 represents an implanted staple before the staple has been brought to near vertical, and FIG. 12 represents an implanted staple after the staple has been brought to near vertical. As can be seen in FIG. 12, the crowning space 98 is smaller after the staple is rotated. Minimizing the crowning space minimizes the possibility that the crown portion 100 of the staple could be caught on an object which would create trauma to the wound site so that healing time is potentially decreased.

By inserting staples at an insertion angle of about 10° and subsequently bringing the staple to near vertical as described, the skin within the grasp of the staple is brought closer together so that the skin is denser than otherwise. This is shown in FIG. 22 by an increased number of striations 102 in the skin. By increasing the skin density in this way, greater anastomosis, or bringing together, of various skin elements is achieved. As a result, skin can grow together more quickly, resulting in shorter post-surgery healing time. Inserting staples at an insertion angle of about 10° also allows the anvil tab 40A of the anvil 40 to disengage the staple more easily, causing less trauma to the wound site.

The stapling device of the present invention comes to the clinician in assembled, loaded and sterilized form. Grasping the device in his or her right or left hand by rearward handle portion 10C and with his or her fingers about trigger member 12 as shown in FIG. 1, the clinician locates the instrument over the wound or incision to be sutured. This is illustrated in FIGS. 9–12 wherein a patient's skin surface 104 is shown containing a wound or incision 106, FIG. 10.

As best shown in FIGS. 9 and 10, the staples of the staple stack 72 are of a channel configuration, with a substantially straight crown portion 100 connecting two 90° elbow regions, from which vertically extend sharpened point prongs or staple legs 112, and 114.

Once the device is properly located over incision 106, FIG. 10, the clinician squeezes trigger member 12 against the action of leaf spring member 48 as shown in FIGS. 1 and 2. As indicated heretofore, pivoting of trigger member 12 in a counterclockwise direction (as viewed in FIGS. 1 and 2) will cause the nose portion 12B of trigger member 12 to shift staple former 44 to its second extended or staple-forming position. As the staple former 44 shifts downwardly, its lowermost edges 44G and 44H, FIGS. 9–11, will contact the crown portion 100 of lead staple 64 to either side of tab 40A of anvil member 40. As the staple former 44 moves further downward, the curved portions 44E and 44F of prongs 44C and 44D will initiate bending of the crown portion 100 of the lead staple 64. Bending may be assisted by tooling marks 108 and 110. This, in turn, will cause staple legs 112 and 114 to enter and be implanted in the skin surface 104, FIGS. 10–11. At the completion of the forming and implanting procedure, the staple will have the configuration shown in FIG. 11, closing incision 106, FIG. 10. It is contemplated to include in an embodiment of the invention a pre-cock position at which point a detent engages and prevents return of the trigger member as described in U.S. Pat. No. 4,669,647 issued to Storace, relevant portions of which relating to a pre-cock position are incorporated herein by reference.

In this configuration, the fully formed and implanted staple 116 is in its post-implantation configuration and is now of such dimension that it can slide off anvil member 40. Upon release of trigger member 12, leaf spring member 48 will return the trigger member to its normal position as shown in FIG. 1. This, in turn, will cause staple former 44 to return to its first retracted or at-rest position. In the meantime, spring 90 and feeder shoe 74 (see FIGS. 15, 18 and 19) will advance the next forwardmost staple of staple stack 72 against the tabs 50J and 50K. As best shown in FIGS. 7 and 17, tabs 50J and 50K align lead staple 64 with first openings 50C and 50D.

Modifications may be made in the invention without departing from the spirit of it. For example, leaf spring member 48 can be replaced by a compression spring or any other appropriate type of biasing means.

The foregoing disclosure and description of the invention are illustrative and explanatory thereof, but to the extent foreseeable, the spirit and scope of the invention are defined by the appended claims.

I claim:

1. A surgical staple cartridge, comprising:
   a housing member having a staple-forming end;
   a staple movably positioned in to housing member along a substantially straight movement path;
   a first opening adjacent the staple-forming end of the housing member to allow access to the staple and a second opening adjacent the staple-forming end of to housing member sized to allow the staple to move through the second opening; and
   a feeder shoe positioned in the housing member for urging the staple along the substantially straight movement path towards the staple-forming end and having a surface angled relative to the staple-forming end of the housing member,
   wherein the feeder shoe moves between an engaged position with the staple-forming end of the housing member and a position away from the staple-forming end of the housing member when pressure is exerted upon the angled surface, and
   wherein the staple, the first opening, and the second opening are substantially vertically oriented at the staple-forming end of the housing member relative to each other and to the movement path of the staple.

2. The surgical staple cartridge of claim 1, further comprising:
   a fixed blocking surface for aligning the staple with the first opening in the staple-forming end of the housing member.

3. The surgical staple cartridge of claim 1, further comprising:
   a staple feeder ramp in the housing member for positioning the staple.

4. The surgical staple cartridge of claim 3, further comprising:
   a fixed blocking surface; and
   the feeder shoe comprising:
   a traveling blocking surface, sized to move along the staple feeder ramp while contacting the fixed blocking surface of the staple cartridge.

5. The surgical staple cartridge of claim 3,
   wherein the feeder shoe has a traveling blocking surface, movably positioned with the staple feeder ramp; and
   the surgical staple cartridge further comprising:
   a fixed blocking surface on the housing member,
   wherein the traveling blocking surface is sized so tat the feeder shoe moves along the staple feeder ramp toward the staple-forming end of the housing member while blocking the staple.

6. The surgical staple cartridge of claim 1, wherein said first opening is sized to provide access to the staple while blocking the staple from moving through said first opening.

7. The surgical staple cartridge of claim 6, wherein said first opening comprises a plurality of openings aligned vertically with the staple and having a blocking member interposed with the plurality of openings.

8. The surgical staple cartridge of claim 1,
   wherein the feeder shoe urges the staple toward the staple-forming end of the housing member.

9. The surgical staple cartridge of claim 8, the feeder shoe comprising:
   a traveling blocking surface, sized to block the staple while moving toward the first opening.

10. The surgical staple cartridge of claim 8, the feeder shoe comprising:
    a traveling blocking surface, adapted to slide along a fixed blocking surface of the housing member to align the staple with the first opening.

11. The surgical staple cartridge of claim 1, further comprising:
    a fixed blocking surface, adapted to align the staple with the first opening; and
    the feeder shoe comprising;
    a traveling blocking surface, sized to block the staple while moving toward the first opening.

12. The surgical staple cartridge of claim 11, wherein the traveling blocking surface slides along the fixed blocking surface.

13. The surgical staple cartridge of claim 1, further comprising
    a cap member, affixed to the housing member after positioning of the staple in the housing member.

14. The surgical staple cartridge of claim 13, further comprising:
    a pusher rod, centrally attached to the cap member.

15. A surgical staple cartridge, comprising:
    a housing member having a staple-forming end;
    a staple movably positioned in the housing member along a substantially straight movement path;
    a first opening adjacent the staple-forming end of the housing member to allow access to the staple and a second opening adjacent the staple-forming end of the housing member sized to allow the staple to move through the second opening;
    a feeder shoe positioned in the housing member and having a surface angled relative to the staple-forming end of the housing member; and
    a flexible arm extending from the housing member and moving between a memory position and a flexed position outwardly from the memory position,
    whereby a greater clearance is provided between the flexible arm and the housing member when the flexible arm is in the flexed position,
    wherein the feeder shoe moves between an engaged position with the staple-forming end of the housing member and a position away from the staple-forming end of the housing member when pressure is exerted upon the angled surface, and
    wherein the staple, the first opening, and the second opening are substantially vertically oriented at the staple-forming end of the housing member relative to each other and to the movement path of the staple.

16. The surgical staple cartridge of claim 15, wherein the flexible arm is proximal to the staple-forming end of the housing member.

17. The surgical staple cartridge of claim 21, wherein housing member flexible arm is biased inward toward a memory position against a side of the housing member.

18. A surgical staple cartridge, comprising:
    a housing member having a staple-forming end comprising;
    a snap receptacle;
    a staple movably positioned in the housing member along a substantially straight movement path;
    a first opening adjacent the staple-forming end of the housing member to allow access to the staple and a second opening adjacent the staple-forming end of the housing member sized to allow the staple to move through the second opening;
    a feeder shoe positioned in the housing member and having a surface angled relative to the staple-forming end of the housing member; and a cap member, affixed to the housing member after positioning of the staple in the housing member, comprising:
- a cap member flexible arm extending from the cap member; and
- a snap, positioned on the cap member flexible arm, the snap removably fixable with the snap receptacle, wherein the feeder shoe moves between an engaged position with the staple-forming end of the housing member and a position away from the staple-farming end of the housing member when pressure is exerted noon the angled surface, and wherein the staple, the first opening, and to second opening are substantially vertically oriented at the staple-forming end of the housing member relative to each other and to the movement path of the staple.

19. The surgical staple cartridge of claim 18, the cap member flexible arm moving between a memory position and a flexed position outwardly from the memory position.

20. The surgical staple cartridge of claim 18, the snap permanently bonded to the snap receptacle, permanently affixing the cap member to the housing member.

21. A surgical staple cartridge, comprising:
a housing member having a staple-forming end comprising:
- a housing member flexible arm; and
- a snap positioned on to housing member flexible arm;

a staple movably positioned in the housing member alone a substantially straight movement path;

a first opening adjacent the staple-forming end of the housing member to allow access to the staple and a second opening adjacent the staple-forming end of the housing member sized to allow to staple to move through to second opening; and a feeder shoe positioned in the housing member and having a surface angled relative to the staple-forming end of the housing member, wherein the feeder shoe moves between an engaged position with the staple-forming end of the housing member and a position away from the staple-forming end of the housing member when pressure is exerted upon the angled surface, and wherein the staple, to first opening and the second opening are substantially vertically oriented at the staple-forming end of tire housing member relative to each other and to the movement path of the staple.

22. The surgical staple cartridge of claim 21, the housing member flexible arm moving between a memory position and a flexed position outwardly from the memory position.

23. A disposable surgical staple cartridge comprising:
a housing member having a fixed staple-forming end;
a feeder shoe positioned in the housing member and having a surface angled relative to the staple-forming end of the housing member;
a staple urged by the feeder shoe towards the staple-forming end along a substantially straight movement path, the staple substantially vertically oriented to the movement path of the staple; and
an opening adjacent the fixed staple-forming end sized to allow the staple to move through the opening, substantially parallel with the staple, wherein the feeder shoe moves between an engaged position with the staple-forming end of the housing member and a position away from the staple-forming end of the housing member when pressure is exerted upon the angled surface.

24. The disposable surgical staple cartridge of claim 23, wherein the staple is blocked by the fixed staple-forming end when positioned for moving through the opening.

25. The disposable surgical staple cartridge of claim 23, wherein the feeder shoe has, a traveling blocking surface, movably positioned with the housing member for urging the staple toward the staple-forming end of the housing member, and
wherein the traveling blocking surface is substantially parallel to the staple.

26. A disposable surgical staple cartridge comprising:
a housing member having a staple-forming end;
a feeder shoe positioned in the housing member and having a surface angled relative to the staple-forming end of the housing member;
a staple of a channel configuration; urged by the feeder shoe towards the staple-forming end along a substantially straight movement path, comprising:
- a substantially straight crown portion;
- a pair of prongs extending orthogonally from the crown portion each prong having a substantially sharpened point on an end opposite the crown portion; and an opening in the staple-forming end sized to allow the staple to move through the opening, wherein the feeder shoe moves between an engaged position with the staple-forming end of the housing member and a position away from the staple-forming end of the housing member when pressure is exerted upon the angled surface.

27. The disposable surgical staple cartridge of claim 26, wherein the pair of prongs are oriented substantially vertically to a movement path of the staple through the housing member.

28. The disposable surgical staple cartridge of claim 26, further comprising:
a cap member, permanently attached to the housing member opposite the staple-forming end after the staple is loaded into the housing member.

29. A surgical staple cartridge, comprising:
a housing member having a staple-forming end; and
a feeder shoe positioned in the housing member for urging the staple alone the substantially straight movement path towards the staple-forming end and having a surface angled relative to the staple-forming end of the housing member, wherein the feeder shoe moves between an engaged position with the staple-forming end of the housing member and a position away from the staple-forming end of the housing member when pressure is exerted upon the angled surface.

30. A surgical staple cartridge, comprising:
a housing member having a staple-forming end; and
a flexible arm extending from the housing member and moving between a memory position and a flexed position outwardly from the memory position, wherein a greater clearance is provided between the flexible arm and the housing member when the flexible arm is in the flexed position.

31. The surgical staple cartridge of claim 30, wherein the flexible arm is proximal to the staple-forming end of the housing member.

32. The surgical staple cartridge of claim 30, wherein the housing member flexible arm is biased inward toward a memory position against a side of the housing member.

* * * * *